(12) United States Patent
Arrieta et al.

(10) Patent No.: US 7,002,681 B1
(45) Date of Patent: Feb. 21, 2006

(54) SPECTROSCOPY SYSTEM FOR THE DETECTION OF CHEMICALS

(75) Inventors: Rodolfo T. Arrieta, Panama City Beach, FL (US); Iris C. Paustian, Panama City, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 331 days.

(21) Appl. No.: 10/602,259

(22) Filed: Jun. 25, 2003

(51) Int. Cl.
*G01J 3/433* (2006.01)
(52) U.S. Cl. .................................. 356/317; 250/459.1
(58) Field of Classification Search ................ 356/317
See application file for complete search history.

(56) References Cited

U.S. PATENT DOCUMENTS 3,768,908 A * 10/1973 Zaromb ..................... 356/301
4,820,046 A * 4/1989 Sohma et al. ............... 356/318
5,633,313 A * 5/1997 Blanchard et al. .......... 356/303
6,180,415 B1 * 1/2001 Schultz et al. .............. 356/317

* cited by examiner

*Primary Examiner*—Gregory J. Toatley, Jr.
*Assistant Examiner*—Kara Geisel
(74) *Attorney, Agent, or Firm*—James T. Shepherd

(57) ABSTRACT

A method of detecting a chemical species at a stand-off distance using a spectroscopy system, the method comprising the steps of providing a modulated light source emitting a first beam of light at a first wavelength incident to the chemical species, the first beam of light causing the chemical species to emit a signal, providing a spectral shifter a second beam of light at a second wavelength, the second beam of light causing a photochemical reaction in the chemical species to shift a spectrum of the light emitted from the chemical species, providing a detector positioned to detect the signal emitted from the chemical species, and providing a data processor system in communication with at least one of the detector and the modulated light source, the data processor system processing the signal to determine the identity of the chemical species.

38 Claims, 4 Drawing Sheets

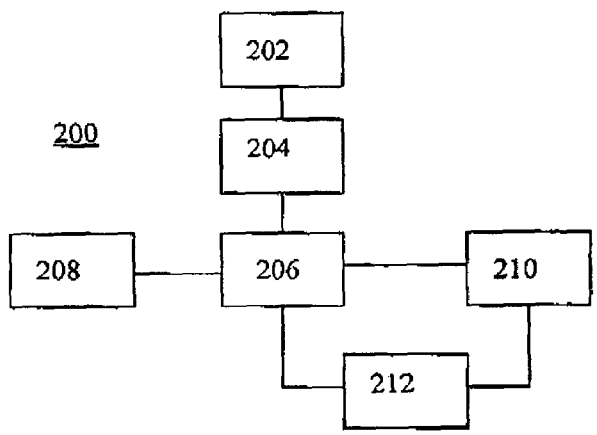

FIG. 3

| STEP | DESCRIPTION |
|------|-------------|
| 202 | Light is directed at chemical species, causing it to emit a signal. |
| 204 | Detector detects signal. |
| 206 | Data processor system attempts to match the spectrum of the signal with a spectrum of a known chemical. |
| 208 | Match is found, chemical species is determined. |
| 210 | No match is found, adjust modulation frequency and return to step 204. |
| 212 | Attempts to match fail, add new spectrum of a known chemical and return to step 206. |

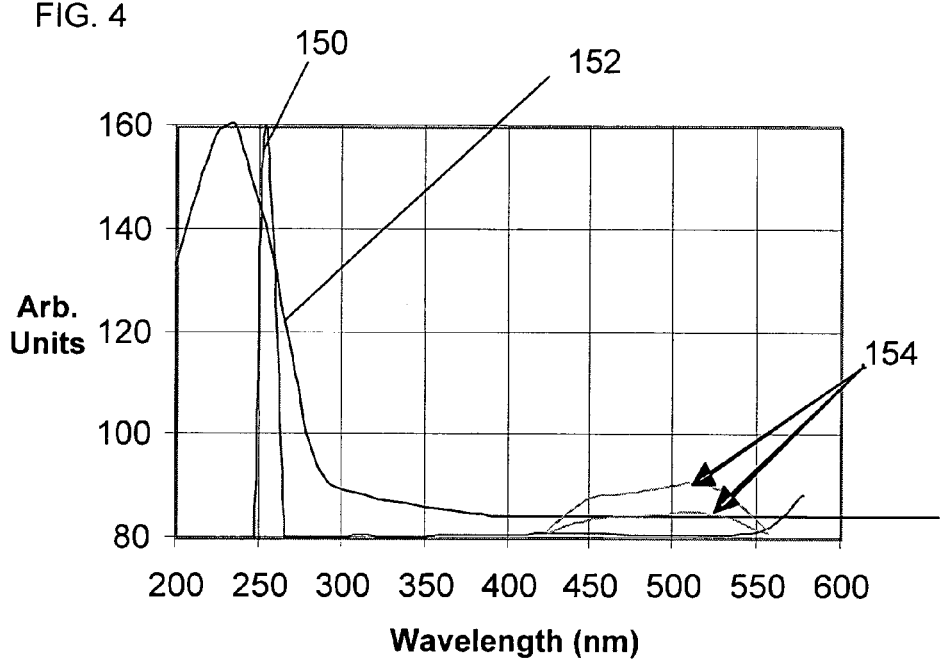

SPECTROSCOPY SYSTEM FOR THE DETECTION OF CHEMICALS

GOVERNMENT RIGHTS

The invention described herein may be manufactured and used by or for the Government of the United State of America for governmental purpose without payment of any royalties thereon or therefor.

BACKGROUND OF THE INVENTION

The present invention generally relates to the detection of a chemical species and, more specifically, to a method and system for detecting and identifying the chemical species using a spectroscopy system.

One major threat to civilian, government and military installations and vehicles is the threat of explosive devices. This threat typically involves an unknown and suspicious structure, such as a package, wherein it is not known whether or not the structure includes an explosive device or harmful chemicals. Hence, nondestructive, stand-off detection of such structures and the detection of contraband high explosives would greatly increase the security of installations and vehicles.

It is well known that explosive devices emit certain chemical species, such as nitroaromatics, or leave an explosive chemical residue on the structure which can be detected to determine the presence of an explosive device. High explosives, especially nitroaromatics, have a complex photochemistry which is based on the excited triplet state of nitroaromatics.

Prior art explosive detection requires physical contact with the structure. For example, in some embodiments, the structure is placed in an instrument to detect the nitroaromatic. In other embodiments, a chemical which reacts with the explosive chemical residue is placed on the structure and then tested. Further, some embodiments use neutron capture and gamma ray detection to detect the presence of the explosive device. However, each of these embodiments requires close physical contact with the structure. Hence, prior art explosive detection is not well suited for detecting nitroaromatics or other harmful chemicals at a safe stand-off distance.

Thus, there is a need in the art for a photoacoustic spectroscopy system which can detect nitroaromatics and other chemical species, at a stand-off distance.

SUMMARY OF THE INVENTION

In one aspect of the present invention, a method and system for detecting a chemical species is disclosed wherein the method includes the steps of providing at least one light source emitting a beam of light incident to the chemical species, the beam of light causing the chemical species to emit a signal and further causing a photochemical reaction to shift a spectrum of the signal emitted by the chemical species, and providing a detector positioned to detect the signal from the chemical species.

In another aspect of the present invention, the chemical species is detected at a stand-off distance and the beam of light includes a first and second wavelength wherein the first wavelength causes the chemical species to emit the signal and the second wavelength causes the photochemical reaction to shift the spectrum of the signal emitted by the chemical species.

These and other features, aspects, and advantages of the present invention will become better understood with reference to the following drawings, description, and claims.

BRIEF DESCRIPTION OF THE DRAWINGS

FIG. 3 illustrates a flow chart of a method of the present invention; and

FIG. 4 illustrates absorption spectra in arbitrary units verses wavelength in nanometers (nm) in accordance with the present invention.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a method and apparatus for detecting a chemical species. Typical chemical species include hazardous or volatile chemicals, as will be discussed presently. In general, the apparatus includes a spectroscopy system with a modulated light source capable of emitting a beam of light at a wavelength $\lambda_1$, the beam of light being incident on the chemical species such that the chemical species emits a signal, a spectral shifter positioned to emit a beam of light at a wavelength $\lambda_2$ to shift a spectrum of the chemical species, a detector positioned to detect the signal from the chemical species, and a data processor system in communication with the detector wherein the data processor system processes the signal and determines the identity of the chemical species. In this manner, the present invention provides a compact and inexpensive spectroscopy system which allows the detection and identification of a chemical species at a safe stand-off distance.

Figure 1:
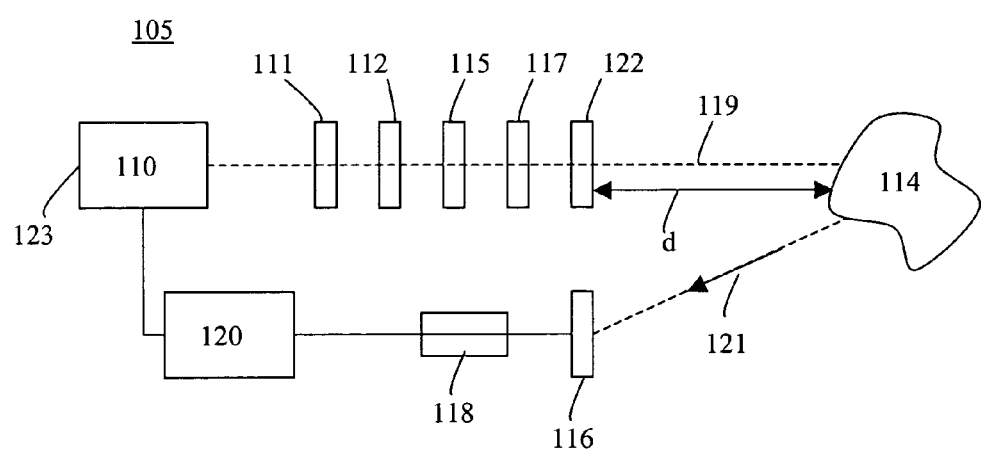
FIG. 1 illustrates a simplified schematic of a photoacoustic spectroscopy system in accordance with the present invention.

Turn now to FIG. 1 which illustrates a spectroscopy system 105 for detecting a chemical species 114 at a stand-off distance, d. It will be understood that the chemical species 114 can include a single element or multiple elements which form a chemical compound. In one embodiment, the system 105 may include a modulated light source 110 that can be capable of emitting light with wavelength $\lambda_1$ along a light path 119, the light being incident on a chemical species 114 such that chemical species 114 may emit a signal 121. Signal 121 may be detected using a detector 116 which may be in communication with a data processor system 120. It will be understood that detector 116 can be in communication with detector 116 through an electrical conductor, an optical fiber, a waveguide, or the like.

Data processor 120 may also be in communication with a modulated light source 110 wherein processor 120 may provide lock-in detection and noise cancellation between the modulated light source 110 and the detector 116 using software programmed into the processor 120. Processor 120 may also process signal 121 to determine the identity of chemical species 114. It will be understood that the signal 121 can include an acoustic signal, an optical signal, or combinations thereof and that detector 116 can include an acoustic detector, a photodetector, or combinations thereof.

In this embodiment, modulated light source 110 may include a 100 W high intensity discharge lamp with a luminous intensity of approximately two Megacandela, wherein a stand-off distance d can be approximately 75 meters. However, it will be understood that the power of light source 110 or spectral shifter 115 may be adjusted as the stand-off distance d is changed (i.e., the power output of at least one of light source 110 or spectral shifter 115 may be increased as d increases).

Also in this embodiment, the light source 110 may be modulated at a frequency to increase a signal-to-noise ratio of the signal 121. For example, in one embodiment, the light source 110 can be modulated at a frequency of 350 Hertz. However, it will be understood that the light source 110 may be modulated at a frequency in a useful range from approximately 10 Hertz to 30000 Hertz, with a preferred range between approximately 10 Hertz to 1000 Hertz. Further, it will be understood that, in alternative embodiments, the light source 110 can include a white light source, a liquid crystal display projector, a xenon flash lamp, a fluorescent light source, a light emitting diode, a gas laser, or a semiconductor laser.

In these alternative embodiments, the modulation may be provided using various methods. For example, if the liquid crystal display projector is included in the light source 110, then the spatial and temporal modulation may be computer controlled. Further, if the xenon flash lamp is included in the light source 110, then the xenon flash lamp may be pulsed with a five to ten microsecond pulsed source, for example. Also, if the fluorescent light source is included in the light source 110, then the fluorescent light source may be intrinsically modulated at a frequency in a range from approximately 18 kHz to 22 kHz. Direct modulation or a chopper (FIG. 2) may be used for the light emitting diode or laser if the light emitting diode or laser is included in the light source 110. It will be understood, however, that these frequencies and methods of modulation are for illustrative purposes only and are not meant to limit the scope of the invention.

As mentioned previously, the chemical species 114 may typically include hazardous or volatile chemicals. For example, the chemical species 114 can include trinitrotoluene (TNT), dinitrotoluene (DNT), nitroaromatics, pesticides, chemical compounds with a Benzene ring, azo compounds, or other chemical species which form colored chemical products (or polymers) photochemically, wherein the colored chemical products generate the signal 121 through the excitation of the chemical species 114 by the light emitted by the light source 110. It will be understood that the spectroscopic bands of interest for the chemical species 114 which cause photochemical reactions are typically in a range from around 200 nm to 400 nm for UV bands, around 400 nm to 700 nm for visible bands, and around 700 nm to 1000 nm for infrared bands. Photochemical reactions are the chemical reactions caused by the interaction of the light emitted by the light source 110 with the chemical species 114.

The visible and near infrared bands of the decomposition products caused by the photochemical reaction of the chemical species 114 may accumulate on a surface of a target or a biofilm to form a residue of material which can be detected. The decomposition products are likely to include highly colored polymeric chromophores similar to synthetic azo dyes. The residue of material can include the decomposition products wherein the infrared bands of the decomposition products are characteristic of several types of N—O and C—N vibrations typically found in explosives. Biofilms include a layered culture of microorganisms which can form on an underwater target, such as a mine or a torpedo.

Generally, the above photochemical reactions can produce Meisenheimer complexes in the decomposition products. Meisenheimer complexes are typically formed by the reaction of a variety of nucleophiles on the aromatic ring of a nitroaromatic compound. The nuclophile may be H—, but the nuclophile may also be OH—, CN—, or carbonyl compounds in other circumstances. Meisenheimer complexes are highly colored (red in the case of OH—TNT), and can either be directly formed and trapped on a substrate such as natural carbonyl containing polymers. Further, a variety of other photointermediates like nitroso toluenes, hydrozylamino toluenes, may also be involved in the formation of the final decomposition products.

In the embodiment illustrated in FIG. 1, a collimator 111 may be positioned on the light path 119 and proximate to the light source 110 to collimate the light emitted by the light source 110. The collimator 111 may be included in this embodiment to redirect and collimate the light emitted from the light source 110. However, it will be understood that, in alternative embodiments, the collimator 111 may be optional wherein the light source 110 already emits collimated light. Further, it will be understood that the collimator 110 may be integrated with the light source 110 in some embodiments.

Also, the positioning of the collimator 111 on the light path 119 is for simplicity and ease of discussion wherein it is understood that the collimator 111 can be otherwise positioned proximate to the light source 110. The positioning of the collimator 111 can depend on the light emitting properties of the light source 110. For example, the collimator 111 can include a parabolic reflector positioned proximate to a side 123 of the light source 110 if the light source 110 is isotropic.

In the embodiment illustrated in FIG. 1, a filter 112 may be positioned proximate to the collimator 111 and on the light path 119 so that the light emitted by the light source 110 flows through the collimator 111 and then the filter 112. Also in this embodiment, a spectral shifter 115 may be positioned on the light path 119 wherein the light emitted from the light source 110 flows therethrough. It will be understood that the positioning of the spectral shifter 115 on the light path 119 is for simplicity and ease of discussion. In this embodiment, the spectral shifter 115 may include a mercury arc lamp with a fused quartz filter. However, it will be understood that the shifter 115 can include an unmodulated ultraviolet light source, a germicidal ultraviolet light source, an electromagnet, or another light source which shifts a spectrum of the signal 121 into a spectral region of modulated light source 110. It will also be understood that the spectral shifter 115 is unmodulated or modulated at frequencies that are much less than the modulation frequency of the modulated light source 110 (i.e., 350 Hertz in this embodiment) so that the spectral shifter 115 minimally contributes to the signal 121, as will be discussed below.

One purpose of the spectral shifter 115 is to create a new absorption spectrum for chemical species 114 that is significantly different from an original absorption spectrum of the same chemical species 114. For example, in some embodiments, the spectral shifter 115 may include a germicidal UV lamp which generates significant radiation in a wavelength range from approximately 250 nm to 285 nm. In low vapor mercury lamps using titanium doped quartz tubing (such as the germicidal UV lamp, mercury arc lamp, etc.), a line at a wavelength of 253.7 nm can be generated.

The spectral shifter 115 may produce a shift in the spectrum of the signal 121 into a spectral region where a filtered output of modulated light source 110 is significant. In this embodiment, the shift in the spectrum may be into any wavelength region where the high intensity discharge lamp included in light source 110 produces significant output. However, it will be understood that the spectral shifter 115 does not have to include an ultraviolet light source. In general, the spectral shifter 115 can include a light source which emits light at a wavelength which shifts the spectrum of the signal 121 wherein the spectral shifter 115 does not generate a significant portion of the signal 121. For example, the spectrum shifter 115 can include a strong electromagnet that produces an electromagnetic field large enough to produce a Zeeman split in a sharp absorption line of an atom included in chemical species 114.

In general, however, the spectral shifter 115 may emit a beam of light with wavelength $\lambda_2$ which can be smaller than or equal to wavelength $\lambda_1$ emitted by the light source 110 wherein wavelength $\lambda_2$ may typically be in an ultraviolet range and wavelength $\lambda_1$ may typically be in a range from infrared to ultraviolet. It should be understood that the beam of light with wavelength $\lambda_1$ can cause chemical species 114 to emit the signal 121 and the beam of light with wavelength $\lambda_2$ can cause the photochemical reaction within chemical species 114 to shift the spectrum of the signal 121.

In the embodiment illustrated in FIG. 1, a filter 117 may be positioned on the light path 119 between the spectral shifter 115 and the chemical species 114. Further, a lens 122 may be positioned between the filter 117 and the chemical species 114. Lens 122 can be positioned to focus the light emitted from the modulated light source 110 onto the chemical species 114. It will be understood that the lens 122 can include a Fresnel lens or the like or, in some embodiments, the light emitted from the modulated light source 110 can be focused using a reflective tube.

The detector 116 is positioned to detect signal 121 emitted from chemical species 114 wherein the detector 116 can include a microphone in communication with a preamplifier 118. It will be understood that the detector 116 can include an optical microphone, a capacitive microphone, a hydrophone (for underwater detection), an optical grating microphone, a photodetector, an imaging device, or another detector capable of detecting the signal 121 emitted from chemical species 114. Further, it will be understood that the preamplifier 118 can be formed as an integral part of detector 116.

In FIG. 1, the data processor system 120 can be in communication with the detector 116 through the preamplifier 118 and the modulated light source 110. In this embodiment, the data processor 120 may provide lock-in detection and noise cancellation (using spectral shifter 115) between the modulated light source 110 and the detector 116 using software programmed into the processor 120. However, it will be understood that lock-in detection can be provided using a lock-in amplifier (not shown).

In the embodiment illustrated in FIG. 1, the modulated light source 110 may be modulated by an AC square wave at 350 Hertz. Signal 121 can be detected by detector 116 and can be amplified by preamplifier 118. The amplified signal may be acquired by the data processor 120 with a sound card wherein the amplified signal is processed using software. The software can be programmed to filter the amplified signal to extract the frequency peaks of the signal.

Further, in this embodiment, noise cancellation can be achieved by turning the spectrum shifter 115 on half way through a data acquisition session wherein the first and the last third of the recorded data are used to calculate the power and phase spectrum of signal 121. Since there can be minimal decomposition products in the first third of the recorded data, the first third of recorded data can be used as a baseline.

Figure 2:
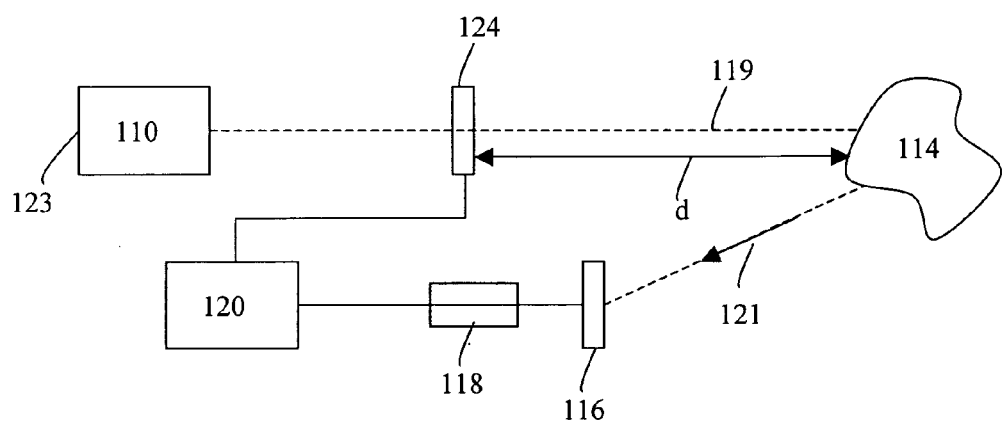
FIG. 2 illustrates a simplified schematic of another embodiment of a photoacoustic spectroscopy system in accordance with the present invention.

Turning now to FIG. 2 which illustrates another embodiment of a spectroscopy system 107 in accordance with the present invention. In FIG. 2, elements similar in function and description to those elements illustrated in FIG. 1 are numbered similarly for simplicity and ease of discussion. In system 107, the light source 110 may include a laser, such as a helium-cadmium (HeCd) laser, an argon (Ar) laser, a dye laser, a semiconductor laser, or combinations thereof, wherein the laser may be modulated by a chopper 124 positioned in the light path 119 and in communication with the data processor 120. In spectroscopy system 107, the light source 110 may provide both the light at wavelength $\lambda_1$ to cause chemical species 114 to emit the signal 121 and the light at wavelength $\lambda_2$ to cause a photochemical reaction to shift the spectrum of the signal 121 of chemical species 114. Further, the chopper 124 may provide lock-in detection between the light source 110 and the detector 116.

With reference to FIG. 3, an embodiment of the present invention includes a method generally designated 200 for detecting and identifying the chemical species 114 as applied to the system 105 illustrated in FIG. 1. It will be understood that a similar method could be applied to the system 107 illustrated in FIG. 2. In a step 202, the light emitted from the light source 110 and the spectral shifter 115 is directed at the chemical species 114 to cause the chemical species 114 to emit the signal 121. In a step 204, the signal 121 is detected by the detector 116 wherein the signal 121 is amplified by the preamplifier 118 and communicated to the data processor system 120. In a step 206, the data processor system 120 is used to determine the identity of the chemical species 114 by matching a spectrum of the signal 121 with a spectrum of a known chemical species. In a step 210, if no match is found by the data processor system 120, then the data processor system 120 adjusts the modulation frequency of the light emitted by the light source 110 to improve a signal-to-noise ratio of signal 121 and the step 204 is repeated until the signal-to-noise ratio is maximized. If the signal-to-noise ratio is maximized in the step 210 and the data processor system still does not identify the chemical species 114, then a new spectrum of a known chemical species is inputted into the data processor system 120 in a step 212 and the step 206 is repeated until a match is found. Once a match is found, the procedure is ended in a step 208 wherein the identity of the chemical species 114 has been determined.

Turning back to FIGS. 1 and 2, spectroscopy systems 105 or 107 can be implemented in several platforms. For example, systems 105 or 107 can be implemented as a portable, battery powered detector which is ideal for detecting explosive threats such as unexploded ordinance, mines, hidden explosives, in-situ forensics, or the like, wherein it is desirable to detect the explosive threat in the field and at a safe stand-off distance. For inspection purposes, the detector 116 may be attached to an object being inspected and then the object can be probed by the modulated light source 110. Since a generated signal can also be transmitted through a medium, the signal 121 can be detected remotely using a directional detector, such as a microphone or a hydrophone (for underwater applications). Further, spectroscopy systems 105 or 107 can also be mounted on an unmanned aerial platform.

EXAMPLES

Turning now to FIG. 4 which illustrates absorption spectra in arbitrary units verses wavelength in nanometers (nm). Shown in FIG. 4 is an absorption spectra 150 for a germicidal lamp, an absorption spectra 152 for TNT, and an absorption spectra 154 for a chemical species formed from a photochemical reaction. The germicidal lamp emits light at a wavelength of 253.7 nm which causes the photochemical reaction to shift the spectra of the TNT to a range from approximately 450 nm to 550 nm. Hence, the germicidal lamp shifts the absorption spectra of the photochemical species away from the TNT absorption spectra so that the chemical species can be identified using known absorption spectra of known chemicals.

It should be understood, of course, that the foregoing relates to preferred embodiments of the invention and that modifications may be made without departing from the spirit and scope of the invention as set forth in the following claims.

We claim:

1. A method of detecting a chemical species using a spectroscopy system, the method comprising the steps of:
   providing at least one light source emitting a beam of light incident to the chemical species, the beam of light causing the chemical species to emit a signal and a photochemical reaction to shift a spectrum of the signal emitted by the chemical species; and
   providing a detector positioned to detect the signal from the chemical species.

2. A method of claim 1, further including a step of providing a data processor system in communication with at least one of the detector and the at least one light source.

3. A method of claim 1, wherein the step of providing the at least one light source emitting the beam of light includes providing the beam of light with a first wavelength and a second wavelength wherein the first wavelength is greater than or equal to the second wavelength.

4. A method of claim 3, wherein the step of providing the first and second wavelengths includes providing the first wavelength in a range from infrared to ultraviolet and providing the second wavelength in an ultraviolet range.

5. A method of claim 4, wherein the first wavelength causes the chemical species to emit the signal and the second wavelength causes the photochemical reaction to shift the spectrum of the light emitted by the chemical species.

6. A method of claim 1, wherein the step of causing the photochemical reaction includes forming colored chemical products which emit the signal.

7. A method of claim 2, wherein the step of identifying the chemical species includes detecting an azo compound.

8. A method of claim 1, wherein the step of providing the at least one light source includes providing at least one of a white light source, a liquid crystal display projector, a xenon flash lamp, a fluorescent light source, a high intensity discharge lamp, a light emitting diode, a gas laser, a semiconductor laser, an unmodulated light source, a mercury arc lamp, a mercury arc lamp with a fused quartz filter, an ultraviolet light source, a germicidal ultraviolet light source, and an electromagnet.

9. A method of claim 1, further including a step of increasing a power output of the at least one light source as a stand-off distance between the chemical species and the spectroscopy system increases.

10. A method of detecting a chemical species at a stand-off distance using a spectroscopy system, the method comprising the steps of:
    providing a first beam of light at a first wavelength incident to the chemical species, the first beam of light causing the chemical species to emit a signal;
    providing a second beam of light at a second wavelength, the second beam of light causing a photochemical reaction in the chemical species to shift a spectrum of the signal emitted by the chemical species;
    providing a detector positioned to detect the signal emitted from the chemical species; and
    providing a data processor system in communication with the detector to process the signal to determine the identity of the chemical species.

11. A method of claim 10, wherein the step of causing the chemical species to emit the signal includes emitting at least one of an acoustic signal and an optical signal.

12. A method of claim 10, wherein the step of detecting the signal emitted from the chemical species includes using at least one of an acoustic detector and a photodetector.

13. A method of claim 10, wherein the step of detecting the signal emitted from the chemical species includes detecting the chemical species wherein the stand-off distance is in a range from approximately 1 meter to 500 meters.

14. A method of claim 10, wherein the step of identifying the chemical species includes detecting at least one of trinitrotoluene (TNT), dinitrotoluene (DNT), a nitroaromatic, a pesticide, a chemical compound with a benzene ring, and a chemical which generates a signal caused by the first beam of light.

15. A method of claim 10, further including a step of modulating the light source at a frequency in a range from approximately 10 Hertz to 30000 Hertz.

16. A method of claim 10, wherein the step of providing the first and second beams of light includes the step of making the first wavelength greater than or equal to the second wavelength.

17. A method of detecting a chemical species at a stand-off distance using a spectroscopy system, the method comprising the steps of:
    providing a modulated light source emitting a first beam of light at a first wavelength incident to the chemical species, the first beam of light causing the chemical species to emit a signal;
    providing a spectral shifter emitting a second beam of light at a second wavelength, the second beam of light causing a photochemical reaction in the chemical species to shift a spectrum of the chemical species;
    providing a detector positioned to detect the signal from the chemical species; and
    providing a data processor system in communication with at least one of the detector and the modulated light source, the data processor system processing the signal to determine the identity of the chemical species.

18. A method of claim 17, further including a step of increasing a power output of at least one of the modulated light source and the spectral shifter as the stand-off distance increases.

19. A method of claim 17, further including a step of providing a lock-in amplifier in communication between the modulated light source and the data processor system.

20. A method of claim 17, wherein the step of providing the detector includes a step of providing at least one of an acoustic detector, a microphone, an optical microphone, a capacitive microphone, a hydrophone, an optical grating microphone, a photodetector, an imaging device, and a detector capable of detecting the signal emitted from the chemical species.

21. A method of claim 17, wherein the step of identifying the chemical species includes detecting an azo compound with at least one of H—, OH—, CN—, a carbonyl compound, and another molecule which forms colored chemical products which emit the signal.

22. The method of claim 17, further including a step of modulating the modulated light source at a frequency in a range from approximately 10 Hertz to 1000 Hertz.

23. A spectroscopy system for detecting a chemical species, the system comprising:
   at least one light source capable of emitting a beam of light incident to the chemical species, the beam of light causing the chemical species to emit a signal and further causing a photochemical reaction to shift a spectrum of the light emitted from the chemical species; and
   a detector positioned to detect the signal emitted from the chemical species.

24. A system of claim 23, wherein a data processor system is in communication with at least one of the detector and the at least one light source, the data processor system processing the signal.

25. A system of claim 23, wherein the at least one light source is capable of emitting the beam of light with a first wavelength and a second wavelength wherein the first wavelength is greater than or equal to the second wavelength.

26. A system of claim 25, wherein the first wavelength is in a range from infrared to ultraviolet and the second wavelength is in an ultraviolet range.

27. A system of claim 26, wherein the first wavelength causes the chemical species to emit the signal and the second wavelength causes the photochemical reaction to shift the spectrum of the chemical species.

28. A system of claim 23, wherein the photochemical reaction forms colored chemical products which emit the signal.

29. A system of claim 23, wherein the chemical species includes an azo compound.

30. A system of claim 23, wherein the at least one light source is modulated at a frequency to increase a signal-to-noise ratio of the signal.

31. A system of claim 23, wherein a power output of the at least one light source is increased as a stand-off distance between the chemical species and the spectroscopy system increases.

32. A spectroscopy system for detecting a chemical species at a stand-off distance, the system comprising:
   a first light source capable of emitting a first beam of light at a first wavelength incident to the chemical species, the first beam of light causing the chemical species to emit a signal;
   a second light source capable of emitting a second beam of light at a second wavelength, the second beam of light causing a photochemical reaction in the chemical species to shift a spectrum of the light emitted from the chemical species;
   a detector positioned to detect the signal emitted from the chemical species; and
   a data processor system in communication with the detector to process the signal to determine the identity of the chemical species.

33. A system of claim 32, wherein the signal emitted from the chemical species includes at least one of an acoustic signal and an optical signal.

34. A system of claim 32, wherein the detector includes at least one of an acoustic detector, a microphone, an optical microphone, a capacitive microphone, a hydrophone, an optical grating microphone, a photodetector, an imaging device, and a detector capable of detecting the signal emitted from the chemical species.

35. A system of claim 32, wherein the chemical species includes at least one of trinitrotoluene (TNT), dinitrotoluene (DNT), a nitroaromatic, a pesticide, a chemical compound with a benzene ring, and a chemical which generates a signal caused by the first beam of light.

36. A system of claim 32, wherein the first light source is modulated at a frequency in a range from approximately 10 Hertz to 30000 Hertz.

37. A system of claim 32, wherein the first light source includes at least one of a white light source, a liquid crystal display projector, a xenon flash lamp, a fluorescent light source, a high intensity discharge lamp, a light emitting diode, a gas laser, and a semiconductor laser.

38. A system of claim 32, wherein the second light source includes at least one of an unmodulated light source, a mercury arc lamp, a mercury arc lamp with a fused quartz filter, an ultraviolet light source, a germicidal ultraviolet light source, an electromagnet, and a light source which shifts a spectrum of the chemical species into a spectral region of the first light source.

* * * * *